United States Patent
Lee (10) Patent No.: US 11,830,227 B2
(45) Date of Patent: Nov. 28, 2023

(54) LEARNING APPARATUS AND LEARNING METHOD FOR THREE-DIMENSIONAL IMAGE

(71) Applicant: Lunit Inc., Seoul (KR)

(72) Inventor: HyunJae Lee, Seoul (KR)

(73) Assignee: LUNIT INC., Seoul (KR)

( * ) Notice: Subject to any disclaimer, the term of this patent is extended or adjusted under 35 U.S.C. 154(b) by 595 days.

(21) Appl. No.: 17/097,036

(22) Filed: Nov. 13, 2020

(65) Prior Publication Data

US 2021/0357694 A1    Nov. 18, 2021

(30) Foreign Application Priority Data

May 12, 2020    (KR) ........................ 10-2020-0056597

(51) Int. Cl.
| | |
|---|---|
| G16H 30/40 | (2018.01) |
| G06N 3/08 | (2023.01) |
| G06F 18/214 | (2023.01) |
| G06F 18/22 | (2023.01) |
| G06V 20/64 | (2022.01) |
| G06N 3/00 | (2023.01) |
| G06V 10/764 | (2022.01) |
| G06V 10/82 | (2022.01) |

(52) U.S. Cl.
CPC .......... *G06V 20/64* (2022.01); *G06F 18/2148* (2023.01); *G06F 18/22* (2023.01); *G06N 3/00* (2013.01); *G06V 10/764* (2022.01); *G06V 10/82* (2022.01); *G16H 30/40* (2018.01); *G06V 2201/03* (2022.01)

(58) Field of Classification Search
None
See application file for complete search history.

(56) References Cited

U.S. PATENT DOCUMENTS

| | | | |
|---|---|---|---|
| 10,643,107 B1 | 5/2020 | Yoo et al. | |
| 2019/0066847 A1* | 2/2019 | Jung | ..................... G06V 20/64 |
| 2019/0073447 A1 | 3/2019 | Guo et al. | |

(Continued)

FOREIGN PATENT DOCUMENTS

| | | |
|---|---|---|
| EP | 3605472 | 2/2020 |
| KR | 10-1894278 | 9/2018 |
| KR | 10-2046134 | 11/2019 |

(Continued)

OTHER PUBLICATIONS

Bolei Zhou et al., "Learning Deep Features for Discriminative Localization", Proceedings of the IEEE conference on computer vision and pattern recognition, 2016.

(Continued)

*Primary Examiner* — Idowu O Osifade
(74) *Attorney, Agent, or Firm* — LEX IP MEISTER, PLLC (57) ABSTRACT

A 3D image sliced into a plurality of slices including the first slice on which a label is annotated and a plurality of second slices on which the label is not annotated is provided as a training sample. A computing device trains a neural network based on the first slice, determines an expandable second slice which is expandable from the first slice from among the plurality of second slices based on the trained neural network; and trains the neural network based on expanded slices including the expandable second slice.

20 Claims, 7 Drawing Sheets

(56) References Cited

U.S. PATENT DOCUMENTS

2021/0334994 A1* 10/2021 Park .................... G06N 20/00

FOREIGN PATENT DOCUMENTS

| KR | 10-2061408 | 12/2019 |
| KR | 10-2020-0002149 | 1/2020 |
| KR | 10-2020-0032651 | 3/2020 |
| KR | 10-2020-0046173 | 5/2020 |
| KR | 10-2144975 | 8/2020 |

OTHER PUBLICATIONS

Ahmet Iscen et al., "Label Propagation for Deep Semi-supervised Learning," arXiv:1904.04717v1 [cs.Cv] (Apr. 9, 2019).

* cited by examiner

LEARNING APPARATUS AND LEARNING METHOD FOR THREE-DIMENSIONAL IMAGE

CROSS-REFERENCE TO RELATED APPLICATION

This application claims priority to and the benefit of Korean Patent Application No. 10-2020-0056597 filed in the Korean Intellectual Property Office on May 12, 2020, the entire contents of which are incorporated herein by reference.

BACKGROUND

(a) Field

The present disclosure relates to a 3D image learning apparatus and learning method.

(b) Description of the Related Art

Supervised learning is a learning strategy in which correct answers are given. The supervised learning is based on the assumption that a correct output for any input is available. Therefore, for the supervised learning, when a dataset is learned, a correct answer about each data of the dataset should be provided.

In a weakly supervised learning environment, however, information on given correct answers is limited. The weakly supervised learning is different from unsupervised learning in which no information is given. However, since only some information is provided, ungiven information should be predicted by learning the given information. For example, when solving a problem of predicting a position of an object in image recognition, it takes a lot of time to annotate positions, but annotating classes of objects can be relatively easy. Therefore, it is possible to learn a learning model that predicts a position of an object in an image by using class information about the objects.

However, such a learning model is only being researched for two-dimensional (2D) images, but not for three-dimensional (3D) images. Particularly, since the 3D image is composed of several slices, annotating a label on the 3D image requires a lot of resources. Therefore, it is necessary to construct a learning model for 3D images with limited annotations.

SUMMARY

An embodiment provides a learning apparatus and a learning method for 3D images in which labels are annotated on some slices.

According to another embodiment, a learning method for 3D images performed by a computing device is provided. The computing device may train a neural network based on a first slice in a 3D image which is sliced into a plurality of slices including the first slice on which a label is annotated and a plurality of second slices on which the label is not annotated. The computing device may determine an expandable second slice which is expandable from the first slice from among the plurality of second slices based on the trained neural network, and train the neural network based on expanded slices including the expandable second slice.

In some embodiments, the computing device may determine a second slice whose similarity with the first slice exceeds a threshold among the plurality of second slices, as the expandable second slice.

In some embodiments, the computing device may calculate the similarity between the first slice and each second slice, based on a first value calculated from the first slice based on the neural network and a second value calculated from each second slice based on the neural network.

In some embodiments, the computing device may extract a feature map from the first slice based on the neural network, and extract a feature map from each second slice based on the neural network. In this case, the first value may include the feature map extracted from the first slice, and the second value may include the feature map extracted from each second slice.

In some embodiments, the computing device may generate a first task output by performing a target task on the first slice in the neural network, and generate a second task output by performing the target task on each second slice in the neural network. In this case, the first value may include the first task output, and the second value may include the second task output.

In some embodiments, the computing device may calculate the similarity based on a cosine similarity between the first value of the first slice and the second value of each second slice.

In some embodiments, the computing device may calculate the similarity based on an L1 distance between the first value of the first slice and the second value of each second slice.

In some embodiments, the computing device may calculate the similarity based on an L2 distance between the first value of the first slice and the second value of each second slice.

In some embodiments, the computing device may assign a label identical to a label of the first slice as a label of the expandable second slice.

In some embodiments, the expanded slices may further include the first slice.

In some embodiments, the expandable second slice may be included in the same 3D image as the first slice.

In some embodiments, the first slice may include two or more slices. In this case, the computing device may determine the expandable second slice from each of the two or more slices.

In some embodiments, the two or more slices may include a slice corresponding to a beginning of a lesion to be annotated with a label and a slice corresponding to an end of the lesion to be annotated with the label among the plurality of slices.

According to yet another embodiment, a learning apparatus for 3D images is provided. The learning apparatus may include a memory and a processor. The memory may store, as a training sample, a 3D image sliced into a plurality of slices including the first slice on which a label is annotated and a plurality of second slices on which the label is not annotated. The processor may train a neural network based on the first slice, determine an expandable second slice which is expandable from the first slice from among the plurality of second slices based on the trained neural network, and train the neural network based on expanded slices including the expandable second slice.

According to still another embodiment, a non-transitory computer-readable medium that stores a program may be provided. The program may configure a computing device to execute training a neural network based on a first slice in a 3D image, the 3D image being sliced into a plurality of slices including the first slice on which a label is annotated and a plurality of second slices on which the label is not annotated, determine an expandable second slice which is expandable from the first slice from among the plurality of second slices based on the trained neural network, and train the neural network based on expanded slices including the expandable second slice.

DETAILED DESCRIPTION OF THE EMBODIMENTS

In the following detailed description, only certain embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification.

As used herein, the singular forms "a", "an" and "the" are intended to include the plural forms as well, unless the context clearly indicates otherwise.

In will be understood that, although the terms first, second, etc., may be used herein to describe various elements, steps and/or operations, these elements, steps and/or operations should not be limited by these terms. Rather, these terms are only used to distinguish one element, step and/or operation from another element, step and/or operation. Thus, a first element, step and/or operation discussed below could be termed as a second element, step and/or operation without departing from the teaching of the present inventive concept.

The sequence of operations or steps is not limited to the order presented in the claims or figures unless specifically indicated otherwise. The order of operations or steps may be changed, several operations or steps may be merged, a certain operation or step may be divided, and a specific operation or step may not be performed.

As used herein, the term "target model" may mean a model that performs a task, and may mean a model to be constructed through machine learning. Since the target model may be implemented based on any machine learning model including a neural network, the technical scope of the present disclosure is not limited by the implementation way of the target model.

As used herein, the term "neural network" encompasses any kind of machine learning model which imitates a neural structure. For example, the neural network may include any kind of neural network-based model, such as an artificial neural network (ANN) and a convolutional neural network (CNN).

Next, a learning method and a learning apparatus according to various embodiments will be described in detail with reference to the accompanying drawings.

Figure 1:
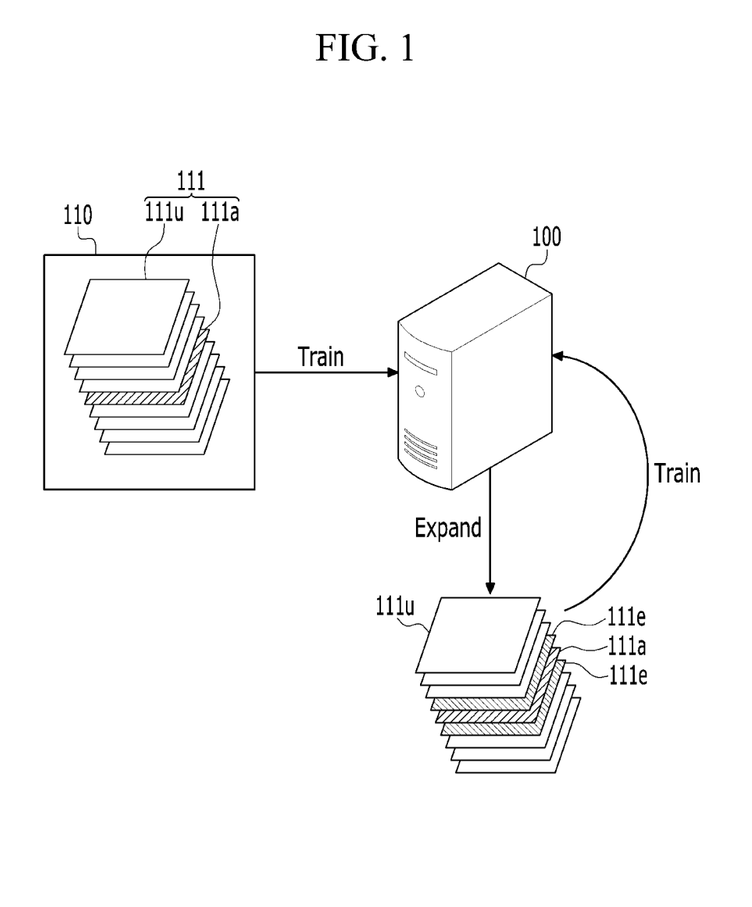
FIG. 1 is a drawing showing a learning apparatus and a learning environment according to an embodiment.
Figure 2:
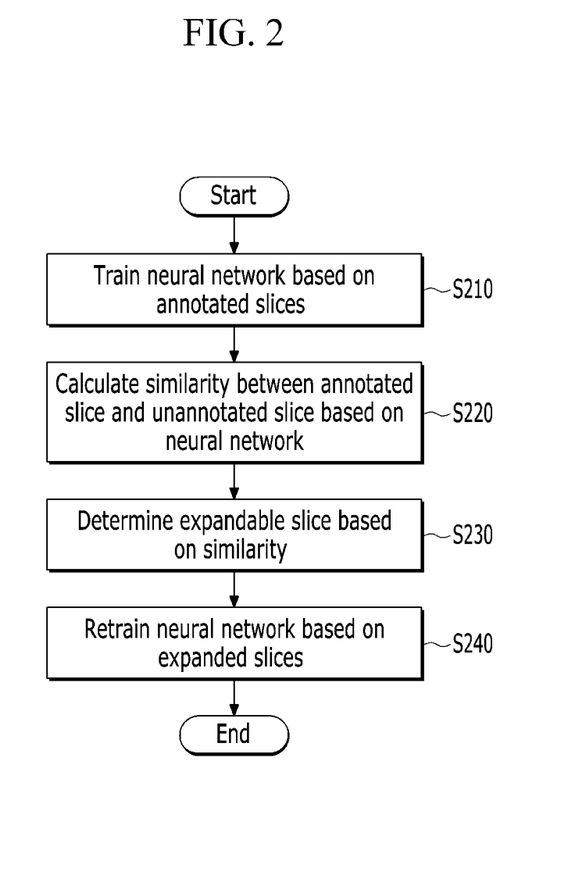
FIG. 2 is a flowchart showing a learning method according to an embodiment.

FIG. 1 is a drawing showing a learning apparatus and a learning environment according to an embodiment, and FIG. 2 is a flowchart showing a learning method according to an embodiment.

Referring to FIG. 1, a learning apparatus 100 is a computing device that performs machine learning on a neural network to perform a target task. In some embodiments, the target task may include a task associated with visual recognition. In one embodiment, the target task may include a task of detecting a lesion from a three-dimensional (3D) image. For example, the 3D image may be a digital breast tomosynthesis (DBT) image or another medical image.

In some embodiments, the computing device may be a tablet computer, a desktop computer, a laptop computer, a server, or the like. However, the computing device is not limited thereto and may include any kind of device having a computing function. An example of the computing device will be described with reference to FIG. 7.

Although FIG. 1 shows the learning apparatus 10 is implemented as one computing device by way of example, in an actual physical environment, functions of the learning apparatus 10 may be implemented by a plurality of computing devices.

The learning apparatus 100 may train a neural network (e.g., a convolutional neural network) using a data set 110 including a plurality of training samples. Each training sample may include a 3D image 111. The 3D image 111 is sliced into a plurality of two-dimensional (2D) frames. Each of 2D frames into which the 3D image 111 is sliced is called a slice. Since it is inefficient to annotate labels on all slices of each 3D image 111 in the data set 100, some slices 111a among the slices are annotated with labels, but some slices 111u are unannotated. Although, for a convenience, FIG. 1 shows an example in which a label is annotated on one slice 111a and the label is not annotated on the remaining slices 111u among the slices of the 3D image, the number of slices annotated with the label is not limited to one. Hereinafter, the slice annotated with the label is referred to as an "annotated slice", and the slice which is not annotated with the label is referred to as an "unannotated slice".

Referring to FIG. 1 and FIG. 2, the learning apparatus 100 trains the neural network based on the annotated slices 111a among the data set 110 at operation S210. In some embodiments, the learning apparatus 100 may predict an object (e.g., a lesion) included in the annotated slice 111a through the neural network, and train the neural network by backpropagating a loss between the predicted result and a label annotated on the slice 111a to the neural network.

The learning apparatus 100 determines an expandable slice among the unannotated slices 111a based on the trained neural network at operations S220 and S230. Since adjacent slices in the 3D image may include a similar lesion at the same position, the learning apparatus 100 may determine a slice having the similar lesion at the same position based on the annotated slice.

In some embodiments, the learning apparatus 100 may calculate a similarity between the annotated slice and each of unannotated slices at operation S220, and determine an unannotated slice 111e whose similarity exceeds a threshold as the expandable slice at operation 230. In some embodiments, the expandable slice may include the unannotated slice included in the same 3D image as the annotated slice. The learning apparatus 100 may expand a range of the annotated slices in the data set 110 by assigning a label identical to the label of the annotated slice to the expandable slice.

The learning apparatus 100 retrains the neural network based on expanded slices 111e of the data set 110 at operation S240. In some embodiments, the expanded slices 111e may include the initially annotated slice 111a as well as the expandable slice. It is difficult to expect an accurate learning effect for the 3D image if the neural network is trained with some slices (for example, one slice) of the 3D image, but the learning effect for the 3D image can be improved by using the expanded slices. Since annotations on some slices in 3D images can be expanded to a larger number of slices than the annotated slices, the time and cost required for the annotation can be reduced. In addition, it is possible to reduce the use of computing resources or network resources required for label annotation.

Figure 3:
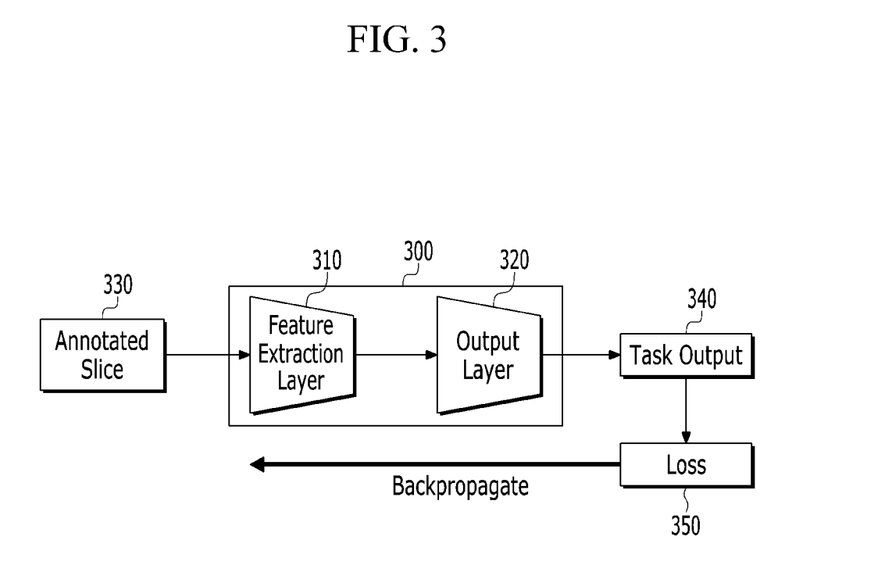
FIG. 3 is a drawing showing a neural network learning process according to an embodiment.

FIG. 3 is a drawing showing a neural network learning process according to an embodiment.

Referring to FIG. 3, a neural network 300 includes a target model, and the target model includes a feature extraction layer 310 and an output layer 320.

An annotated slice 330 among a plurality of slices of each 3D image of a data set is input to the feature extraction layer 310. The feature extraction layer 310 extracts features from the annotated slice 330. Such features may be expressed in the form of a feature map.

In some embodiments, the feature extraction layer 310 may include a plurality of layers. A first layer among the plurality of layers may receive an input image and extract a feature map from the input image. The other layers may extract a feature map again from the feature map transmitted by the previous layer and transfer the extracted feature map to the next layer. In some embodiments, each layer may extract a feature map by applying an operation of the corresponding layer to the input image or input feature map.

In some embodiments, the feature extraction layer 310 may include a convolutional layer. The convolutional layer may extract a feature map by applying a convolution filter to the input image or input feature map. The convolution filter may extract a feature map by performing a convolution operation on a receptive field of the input image or input feature map.

In some embodiments, the feature extraction layer 310 may further include other layers such as a pooling layer and an activation layer. The pooling layer can extract features by performing a pooling operation on input features. The activation layer is a layer that performs non-linear transformation on input data through an activation function, and may include a sigmoid function, a rectified linear unit (ReLU) function, or the like.

The output layer 320 generates a task output 340 according to the target task based on the feature map extracted from the feature extraction layer 310. In some embodiments, the task output 340 may include a predicted value indicating an object (e.g., a lesion) predicted by the target model. In some embodiments, the output layer 320 may include a fully connected layer that performs classification from a feature map that is output through the feature extraction layer 310. In some embodiments, a plurality of fully connected layers may be provided.

A loss 350 between the task output 340 of the output layer 320 and a label annotated on an input slice is calculated, and the loss 350 is backpropagated to the neural network 300 so that the neural network 300 is trained. In some embodiments, the neural network 300 may be trained by updating learnable parameters used in the neural network 300. In some embodiments, the learnable parameters may include weights used in each layer of the neural network 300.

Figure 4:
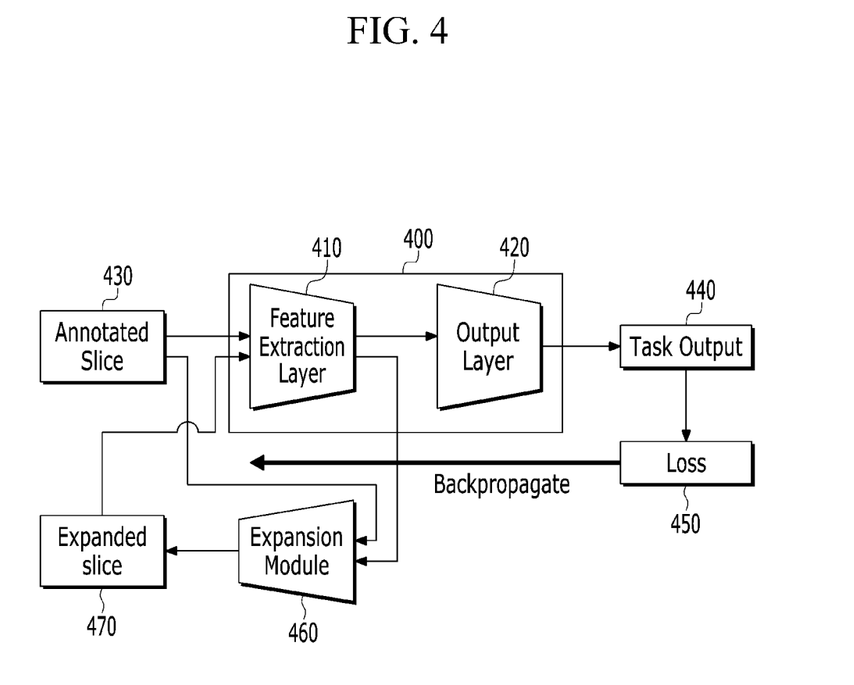
FIG. 4 and FIG. 5 are drawings showing an expansion process according to various embodiments.
Figure 5:
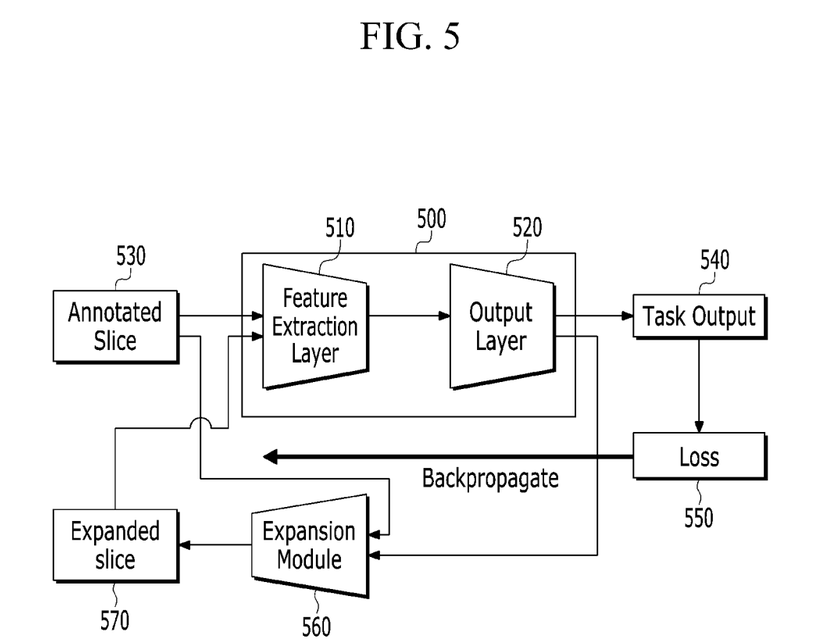

FIG. 4 and FIG. 5 are drawings showing an expansion process according to various embodiments.

Referring to FIG. 4, a neural network 400 includes a target model, and the target model includes a feature extraction layer 410 and an output layer 420. Since the feature extraction layer 410 and the output layer 420 perform the similar operations as those of the feature extraction layer 310 and the output layer 320 described with reference to FIG. 3, their detailed descriptions are omitted.

The feature extraction layer 410 extracts features from each 3D image of training samples. Such features may be expressed in the form of a feature map. The feature extraction layer 410 extracts a feature map from an annotated slice of each 3D image, and extracts feature maps from unannotated slices.

An expansion module 460 calculates a similarity between the feature map of the annotated slice and the feature map of each unannotated slice. Hereinafter, the annotated slice is referred to as a "target slice". In some embodiments, when there is an unannotated slice whose similarity with the target slice exceeds a threshold, the expansion module 460 may determine the unannotated slice with the similarity exceeding the threshold as an expandable slice of the target slice. In some embodiments, the expansion module 460 may search for the expandable slice 570 from unannotated slices belonging to the same 3D image as the target slice.

In some embodiments, the expansion module 460 may calculate the similarity between the target slice and the unannotated slice based on a cosine similarity. In one embodiment, the expansion module 460 may calculate a similarity $S_c(A,U)$ for a feature map of each of unannotated slices to compare the similarity with the feature map of the target slice, as in Equation 1, and compare the calculated similarity $S_c(A,U)$ with a threshold. In this case, since the similarity $S_c(A,U)$) increases as the similarity between the target slice and the unannotated slice increases, the expansion module 460 may determine the unannotated slice whose similarity $S_c(A,U)$ exceeds (e.g., is greater than, or is equal to or greater than) the threshold as the expandable slice 470.

$$S_c(A, U) = \frac{A \cdot B}{\|A\|\|B\|} = \frac{\Sigma_{i,j} A_{i,j} U_{i,j}}{\sqrt{\Sigma_{i,j} A_{i,j}^2} \sqrt{\Sigma_{i,j} U_{i,j}^2}} \quad \text{Equation 1}$$

In Equation 1, $A_{i,j}$ denotes a vector of a spatial position (i,j) in the feature map of the annotated slice, and $U_{i,j}$ denotes a vector of a spatial position (i,j) in the feature map of the unannotated slice.

In some embodiments, the expansion module 460 may calculate the similarity between the target slice and the unannotated slice based on a cosine distance. In one embodiment, the expansion module 460 may calculate the similarity based on the cosine distance $D_c(A,U)$ obtained by subtracting the cosine similarity from one (1), as in Equation 2.

$$D_c(A, U) = 1 - S_c(A, U) = 1 - \frac{\Sigma_{i,j} A_{i,j} U_{i,j}}{\sqrt{\Sigma_{i,j} A_{i,j}^2} \sqrt{\Sigma_{i,j} U_{i,j}^2}} \quad \text{Equation 2}$$

In some embodiments, the expansion module 460 may calculate the similarity between the target slice and the unannotated slice based on an Lp distance. In one embodiment, the expansion module 460 may calculate an L1 distance between the target slice and the unannotated slice as the similarity. In this case, the expansion module 460 may calculate the L1 distance L1(A,U) for the feature map of each of the unannotated slices to compare the similarity with the feature map of the target slice, as in Equation 3, and compare the calculated L1 distance L1(A,U) with the threshold. In another embodiment, the expansion module 460 may calculate an L2 distance between the target slice and the unannotated slice as the similarity. In this case, the expansion module 460 may calculate the L2 distance L2(A, U) for the feature map of each of the unannotated slices to compare the similarity with the feature map of the target slice, as in Equation 4, and compare the calculated L2 distance L2(A,U) with the threshold. In this case, since the Lp distance decreases as the similarity between the target slice and the unannotated slice increases, the expansion module 460 may determine an unannotated slice whose Lp distance is exceeds (i.e., less than, or is equal to less than) the threshold as the expandable slice 470.

$$L1(A, U) = \|A - U\| = \sum_{i,j} |A_{i,j} - U_{i,j}| \quad \text{Equation 3}$$

$$L2(A, U) = \|A - U\|_2 = \sqrt{\sum_{i,j} (A_{i,j} - U_{i,j})^2} \quad \text{Equation 4}$$

In Equations 3 and 4, $A_{i,j}$ denotes a vector of a spatial position (i,j) in the feature map of the annotated slice, and $U_{i,j}$ denotes a vector of a spatial position (i,j) in the feature map of the unannotated slice.

As such, the expansion module 460 may select the unannotated slice whose similarity with the target slice exceeds the threshold (e.g., the similarity is greater than, or equal to or greater than the threshold) as the expandable slice 470 and then determine a label of the expandable slice based on a label of the target slice, thereby expanding annotated slices. In some embodiments, the label of the expandable slice 470 may be set to be identical to the label of the target slice.

The expansion module 460 inputs expandable slices (hereinafter referred to as "expanded slices") 470 whose labels are set to the neural network 400 in order to retrain the neural network. In some embodiments, the expanded slice 470 may further include the target slice. Accordingly, the feature extraction layer 410 extracts a feature map from the expanded slice 470, and the output layer 420 generates a task output 440 based on the feature map extracted in the feature extraction layer 410. A loss 450 between the task output 440 predicted in the output layer 420 and the label annotated on the expanded slice 470 input to the neural network 400 is calculated, and the loss 450 is backpropagated to the neural network 400 so that the neural network 400 can be further trained.

Referring to FIG. 5, a neural network 500 includes a target model, and the target model includes a feature extraction layer 510 and an output layer 520. Since the feature extraction layer 510 and the output layer 520 perform the similar operations as those of the feature extraction layer 310 and the output layer 320 described with reference to FIG. 3, their detailed descriptions are omitted.

The feature extraction layer 510 extracts features from each 3D image of training samples. Such features may be expressed in the form of a feature map. The feature extraction layer 510 extracts a feature map from an annotated slice of each 3D image, and extracts feature maps from unannotated slices.

The output layer 520 generates a task output based on the feature map extracted from the annotated slice, and also generates a task output based on the feature map extracted from the unannotated slice.

An expansion module 560 calculates a similarity between the task output of the annotated slice and the task output of each unannotated slice. In some embodiments, when there is an unannotated slice whose similarity with the target slice exceeds a threshold, the expansion module 560 may determine the unannotated slice whose similarity with the target slice exceeds (e.g., is greater than, or is equal to or greater than) the threshold as the expandable slice 570 of the target slice. In some embodiments, the expansion module 560 may search for the expandable slice 570 from unannotated slices belonging to the same 3D image as the target slice.

In some embodiments, the expansion module 560 may calculate the similarity between the target slice and the unannotated slice based on a cosine similarity. In one embodiment, the expansion module 560 may calculate a similarity for a task output of each of unannotated slices to compare the similarity with the task output of the target slice, as in Equation 1, and compare the calculated similarity with a threshold.

In some embodiments, the expansion module 560 may calculate the similarity between the target slice and the unannotated slice based on a cosine distance. In one embodiment, the expansion module 560 may calculate the cosine distance by subtracting the cosine similarity from one (1), and compare calculate the cosine distance with the similarity.

In some embodiments, the expansion module 560 may calculate the similarity between the target slice and the unannotated slice based on an Lp distance. In one embodiment, the expansion module 560 may calculate the similarity based on an L1 distance between the target slice and the unannotated slice. In this case, the expansion module 560 may calculate the L1 distance for the task output of each of the unannotated slices to compare the similarity with the task output of the target slice, as in Equation 3, and compare the calculated L1 distance with the threshold. In another embodiment, the expansion module 560 may calculate the similarity based on an L2 distance between the target slice and the unannotated slice. In this case, the expansion module 560 may calculate the L2 distance for the task output of each of the unannotated slices to compare the similarity with the task output of the target slice, as in Equation 4, and compare the calculated L2 distance with the threshold.

As such, the expansion module 560 may select the unannotated slice whose similarity with the target slice exceeds the threshold as the expandable slice 570, and then determine a label of the expandable slice 570 based on the label of the target slice, thereby expanding annotated slices. In some embodiments, the label of the expandable slice 570 may be set to be identical to the label of the target slice.

The expansion module 560 retrains the neural network by inputting the expanded slice 570 whose labels are set to the neural network 500. In some embodiments, the expanded slice 570 may further include the target slice.

Accordingly, the feature extraction layer 510 extracts a feature map from the expanded slice, and the output layer 520 generates a task output 540 based on the feature map extracted in the feature extraction layer 510. A loss 550 between the task output 540 predicted in the output layer 520 and the label annotated on the expanded slice 570 input to the neural network 500 is calculated, and the loss 550 is backpropagated to the neural network 500 so that the neural network 500 can be further trained.

Although an example in which a label is annotated on one slice of a 3D image has been described, a label may be annotated on two or more slices of the 3D image. In this case, an expandable slice can be determined from each of the two or more slices. A learning method using the two or more annotated slices is described below.

Figure 6:
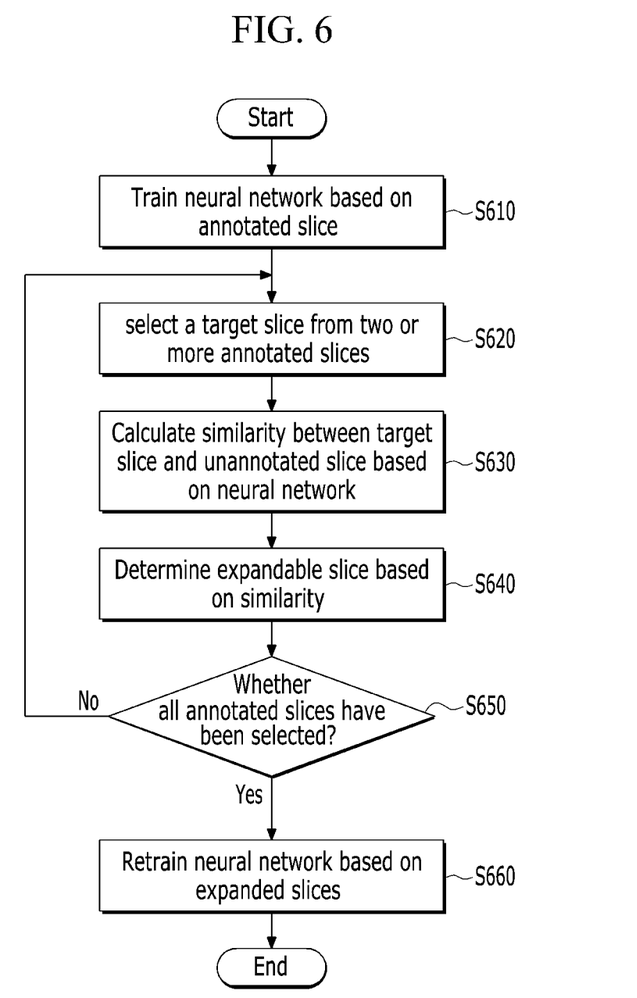
FIG. 6 is a flowchart showing a learning method according to another embodiment.

FIG. 6 is a flowchart showing a learning method according to another embodiment.

Referring to FIG. 6, a learning apparatus trains a neural network based on an annotated slice among the data set at operation S610. In some embodiments, the learning apparatus 100 may predict an object (e.g., a lesion) included in the annotated slice through the neural network, and train the neural network by backpropagating a loss between the predicted result and a label annotated on the slice to the neural network.

The learning apparatus determines an expandable slice from each of the annotated slices of the 3D image based on the trained neural network at operations S620, S630, S640, and S650. In some embodiments, the learning apparatus may select a target slice from two or more annotated slices of the 3D image at operation S620, calculate a similarity between the selected target slice and the unannotated slice at operation S630, and determine the unannotated slice whose similarity with the target slice exceeds a threshold as an expandable slice at operation S640. In some embodiments, the learning apparatus may expand the annotated slice by assigning a label identical to the label of the selected annotated slice to the determined expandable slice.

If the expandable slice has not been determined for all the annotated slices of the 3D image at operation S650, the learning apparatus may select another target slice from the two or more annotated slices of the 3D image, and repeat operations S630, S640, and S650 of determining the expandable slice from the selected target slice. Accordingly, the annotated slices can be expanded based on the two or more slices on which the label is annotated in the 3D image.

The learning apparatus retrains the neural network based on the expanded slices of the data set at operations S660. When annotated slices are widely expanded based on one slice, there may be an expanded slice that adversely affects machine learning. However, when annotated slices are narrowly expanded based on each of two or more slices, an expanded slice that adversely affects the machine learning can be eliminated.

In some embodiments, the two or more slices may include a slice corresponding to the beginning of a lesion and a slice corresponding to the end of the lesion. In this case, the expanded slice adversely affecting the machine learning can be eliminated by expanding the annotated slice based on the slice corresponding to the beginning of the lesion and expanding the annotated slice based on the slice corresponding to the end of the lesion.

Hereinafter, an example computing device 700 for implementing a learning apparatus or a leaning method according to an embodiment is described with reference to FIG. 7.

Figure 7:
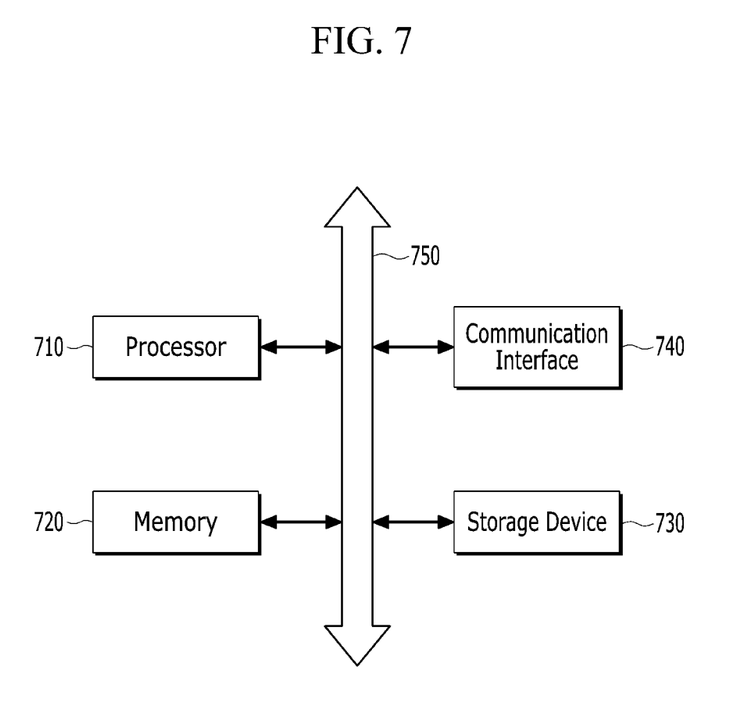
FIG. 7 is a drawing showing an example computing device according to an embodiment.

FIG. 7 is a drawing showing an example computing device according to an embodiment.

Referring to FIG. 7, a computing device 700 includes a processor 710, a memory 720, a storage device 730, a communication interface 740, and a bus 750. The computing device 700 may further include other general components.

The processor 710 control overall operation of each component of the computing device 700. The processor 710 may be implemented with at least one of various processing units such as a central processing unit (CPU), a microprocessor unit (MPU), a micro controller unit (MCU), and a graphic processing unit (GPU), or may be implemented with parallel processing units. In addition, the processor 710 may perform operations on a program for executing the above-described learning method for 3D images.

Memory 720 stores various data, commands, and/or information. The memory 720 may load a computer program from the storage device 730 to execute the above-described learning method for 3D images. The storage device 730 may non-temporarily store the program. The storage device 730 may be implemented as a nonvolatile memory.

The communication interface 740 supports wired or wireless Internet communication of the computing device 700. In addition, the communication interface 740 may support various communication methods other than the Internet communication.

The bus 750 provides a communication function between components of the computing device 700. The bus 750 may be implemented as various types of buses such as an address bus, a data bus, and a control bus.

The computer program may include instructions that cause the processor 710 to perform the learning method for 3D images when loaded into the memory 720. That is, the processor 710 may perform operations for the learning method for 3D images by executing the instructions.

In some embodiments, the computer program may include instructions of training a neural network based on a first slice in a 3D image, the 3D image being sliced into a plurality of slices including the first slice on which a label is annotated and a plurality of second slices on which the label is not annotated, determining an expandable second slice which is expandable from the first slice from among the plurality of second slices based on the trained neural network, and training the neural network based on expanded slices including the expandable second slice.

The learning method or learning apparatus for 3D images according to an embodiment described above may be implemented as a computer-readable program on a computer-readable medium. In one embodiment, the computer-readable medium may include a removable recording medium or a fixed recording medium. In another embodiment, the computer-readable program recorded on the computer-readable medium may be transmitted to another computing device via a network such as the Internet and installed in another computing device, so that the computer program can be executed by another computing device.

While this invention has been described in connection with what is presently considered to be practical embodiments, it is to be understood that the invention is not limited to the disclosed embodiments. On the contrary, it is intended to cover various modifications and equivalent arrangements included within the spirit and scope of the appended claims.

What is claimed is:

1. A learning method for three-dimensional (3D) images performed by a computing device, comprising:
    training a neural network based on a first slice in a 3D image, the 3D image being sliced into a plurality of slices including the first slice on which a label is annotated and a plurality of second slices on which the label is not annotated;
    determining an expandable second slice which is expandable from the first slice from among the plurality of second slices based on the trained neural network; and
    training the neural network based on expanded slices including the expandable second slice.

2. The learning method of claim 1, wherein the determining the second slice comprises determining a second slice whose similarity with the first slice exceeds a threshold among the plurality of second slices, as the expandable second slice.

3. The learning method of claim 2, further comprising calculating the similarity between the first slice and each second slice, based on a first value calculated from the first slice based on the neural network and a second value calculated from each second slice based on the neural network.

4. The learning method of claim 3, further comprising:
extracting a feature map from the first slice based on the neural network; and
extracting a feature map from each second slice based on the neural network,
wherein the first value includes the feature map extracted from the first slice, and the second value includes the feature map extracted from each second slice.

5. The learning method of claim 3, further comprising:
generating a first task output by performing an target task on the first slice in the neural network; and
generating a second task output by performing the target task on each second slice in the neural network,
wherein the first value includes the first task output, and the second value includes the second task output.

6. The learning method of claim 3, wherein the calculating the similarity comprises calculating the similarity based on a cosine similarity between the first value of the first slice and the second value of each second slice.

7. The learning method of claim 3, wherein the calculating the similarity comprises calculating the similarity based on an L1 distance between the first value of the first slice and the second value of each second slice.

8. The learning method of claim 3, wherein the calculating the similarity comprises calculating the similarity based on an L2 distance between the first value of the first slice and the second value of each second slice.

9. The learning method of claim 1, further comprising assigning a label identical to a label of the first slice as a label of the expandable second slice.

10. The learning method of claim 1, wherein the expanded slices further include the first slice.

11. The learning method of claim 1, wherein the expandable second slice is included in a same 3D image as the first slice.

12. The learning method of claim 1, wherein the first slice includes two or more slices, and
wherein the determining the expandable second slice includes determining the expandable second slice from each of the two or more slices.

13. The learning method of claim 12, wherein the two or more slices include a slice corresponding to a beginning of a lesion to be annotated with a label and a slice corresponding to an end of the lesion to be annotated with the label among the plurality of slices.

14. A learning apparatus for three-dimensional (3D) images, comprising:
a memory that stores, as a training sample, a 3D image sliced into a plurality of slices including the first slice on which a label is annotated and a plurality of second slices on which the label is not annotated; and
a processor that trains a neural network based on the first slice, determines an expandable second slice which is expandable from the first slice from among the plurality of second slices based on the trained neural network; and trains the neural network based on expanded slices including the expandable second slice.

15. The learning apparatus of claim 14, wherein the processor determines, as the expandable second slice, a second slice whose similarity with the first slice exceeds a threshold among the plurality of second slices.

16. The learning apparatus of claim 15, wherein the processor calculates similarity between the first slice and each second slice based on a first value calculated from the first slice based on the neural network and a second value calculated from each second slice based on the neural network.

17. The learning apparatus of claim 16, wherein the processor extracts a feature map from the first slice based on the neural network, and extracts a feature map from each second slice based on the neural network,
wherein the first value includes the feature map extracted from the first slice, and the second value includes the feature map extracted from each second slice.

18. The learning apparatus of claim 16, wherein the processor generates a first task output by performing a target task on the first slice in the neural network, and generates a second task output by performing the target task on each second slice in the neural network,
wherein the first value includes the first task output, and the second value includes the second task output.

19. The learning apparatus of claim 14, wherein the processor assigns a label identical to a label of the first slice as a label of the expandable second slice.

20. A non-transitory computer-readable medium that stores a program for configuring a computing device to execute:
training a neural network based on a first slice in a three-dimensional (3D) image, the 3D image being sliced into a plurality of slices including the first slice on which a label is annotated and a plurality of second slices on which the label is not annotated;
determining an expandable second slice which is expandable from the first slice from among the plurality of second slices based on the trained neural network; and
training the neural network based on expanded slices including the expandable second slice.

* * * * *